(12) United States Patent
Garcia Molina et al.

(10) Patent No.: US 11,116,935 B2
(45) Date of Patent: Sep. 14, 2021

(54) SYSTEM AND METHOD FOR ENHANCING SENSORY STIMULATION DELIVERED TO A USER USING NEURAL NETWORKS

(71) Applicant: KONINKLIJKE PHILIPS N.V., Eindhoven (NL)

(72) Inventors: Gary Nelson Garcia Molina, Madison, WI (US); Sander Theodoor Pastoor, Vleuten (NL); Ulf Grossekathöfer, Eindhoven (NL); Erik Bresch, Eindhoven (NL); Adrienne Heinrich, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 313 days.

(21) Appl. No.: 16/407,777

(22) Filed: May 9, 2019

(65) Prior Publication Data

US 2019/0344042 A1    Nov. 14, 2019

Related U.S. Application Data

(60) Provisional application No. 62/669,526, filed on May 10, 2018, provisional application No. 62/691,269, filed on Jun. 28, 2018.

(51) Int. Cl.
*A61M 21/02* (2006.01)
*A61B 5/0476* (2006.01)
(Continued)

(52) U.S. Cl.
CPC ............ *A61M 21/02* (2013.01); *A61B 5/369* (2021.01); *A61B 5/4812* (2013.01);
(Continued)

(58) Field of Classification Search
CPC .......... G06N 3/0445; G06N 3/08; A61M 2021/0022; A61M 2021/0044;
(Continued)

(56) References Cited

U.S. PATENT DOCUMENTS 10,098,582 B1 * 10/2018  McNair ............... A61B 5/4812
10,137,276 B2    11/2018  Garcia Molina et al.
(Continued)

FOREIGN PATENT DOCUMENTS

WO    2012138761 A1    10/2012
WO    2015092591 A1    6/2015

OTHER PUBLICATIONS

H.-V. V Ngo, A. Miedema, I. Faude, T. Martinetz, M. Molle, and J. Born, "Driving Sleep Slow Oscillations by Auditory Closed-Loop Stimulation—A Self-Limiting Process," J. Neurosci., vol. 35, No. 17, pp. 6630-6638, 2015.

(Continued)

*Primary Examiner* — Christine H Matthews
*Assistant Examiner* — Joshua Daryl D Lannu

(57) ABSTRACT

The present disclosure pertains to a system and method for delivering sensory stimulation to a user during a sleep session. The system comprises one or more sensors, one or more sensory stimulators, and one or more hardware processors. The processor(s) are configured to: determine one or more brain activity parameters indicative of sleep depth in the user based on output signals from the sensors; cause a neural network to indicate sleep stages predicted to occur at future times for the user during the sleep session; cause the sensory stimulator(s) to provide the sensory stimulation to the user based on the predicted sleep stages over time during the sleep session, and cause the sensory stimulator(s) to modulate a timing and/or intensity of the sensory stimulation based on the one or more brain activity parameters and (Continued)

values output from one or more intermediate layers of the neural network.

21 Claims, 10 Drawing Sheets

(51) Int. Cl.
*A61B 5/00* (2006.01)
*G06N 3/08* (2006.01)
*G06N 3/04* (2006.01)
*G16H 20/70* (2018.01)
*A61B 5/369* (2021.01)
*A61M 21/00* (2006.01)

(52) U.S. Cl.
CPC ......... *A61B 5/7267* (2013.01); *G06N 3/0445* (2013.01); *G06N 3/08* (2013.01); *G16H 20/70* (2018.01); *A61M 2021/0027* (2013.01); *A61M 2205/50* (2013.01); *A61M 2230/10* (2013.01)

(58) Field of Classification Search
CPC .............. A61M 2230/04; A61M 21/00; A61M 2205/50; A61M 2230/10; A61M 2021/0072; A61M 2205/3553; A61M 2205/332; A61M 2205/3592; A61M 2230/50; A61M 2205/3306; A61M 2021/0055; A61M 2021/0027; A61M 2230/63; A61M 2205/502; A61M 2230/205; A61M 2230/06; A61M 2230/14; A61M 2209/088; A61M 2205/3584; A61M 2021/0016; A61M 2230/40; A61M 21/02; A61M 2205/3569; A61M 2205/3375; A61M 2230/005; A61B 5/7267; A61B 5/02416; A61B 5/0006; A61B 5/374; A61B 2562/0219; A61B 5/6824; A61B 5/6829; A61B 5/0022; A61B 5/369; A61B 5/4812; G16H 20/70; G16H 50/20; G16H 40/60; A61N 1/36025

See application file for complete search history.

(56) References Cited

U.S. PATENT DOCUMENTS

| | | |
|---|---|---|
| 10,183,142 B2 | 1/2019 | Garcia Molina et al. |
| 10,220,183 B2 | 3/2019 | Garcia Molina et al. |
| 2014/0221779 A1 | 8/2014 | Schoonover |
| 2016/0296164 A1 | 10/2016 | Garcia Molina |
| 2016/0302718 A1 | 10/2016 | Laura Lapoint et al. |
| 2017/0055899 A1* | 3/2017 | Bandyopadhyay .... A61B 5/743 |
| 2018/0064388 A1* | 3/2018 | Heneghan ................ A61B 5/11 |
| 2018/0238103 A1* | 8/2018 | Jensen .................. E06B 3/6775 |
| 2020/0222699 A1* | 7/2020 | de Zambotti ......... A61M 21/00 |

OTHER PUBLICATIONS

M. Bellesi, B. Riedner, G. Garcia-Molina, C. Cirelli, and G. Tononi, "Enhancement of sleep slow waves: underlying mechanisms and practical consequences," Front Syst. Neurosci., vol. 8, No. October, pp. 1-17, Oct. 2014.

J. Carrier, I. Viens, G. Poirier, R. Robillard, M. Lafortune, G. Vandewalle, N. Martin, M. Barakat, J. Paquet, and D. Filipini, "Sleep slow wave changes during the middle years of life," Eur. J. Neurosci., vol. 33, No. 4, pp. 758-766, 2011.

J. Carrier, S. Land, D. J. Buysse, D. J. Kupfer, and T. H. Monk, "The effects of age and gender on sleep EEG power spectral density in the middle years of life (ages 20-60 years old).," Psychophysiology, vol. 38, No. 2, pp. 232-242, 2001.

H. Merica and R. D. Fortune, "A neuronal transition probability model for the evolution of power in the sigma and delta frequency bands of sleep EEG.," Physiol. Behav., vol. 62, No. 3, pp. 585-589, Sep. 1997.

K. Susmáková and A. Krakovská, "Discrimination ability of individual measures used in sleep stages classification.," Artif. Intell. Med., vol. 44, No. 3, pp. 261-277, Nov. 2008.

International Search Report and Written Opinion, International Application No. PCT/EP2019/061990, dated May 9, 2019.

* cited by examiner

SYSTEM AND METHOD FOR ENHANCING SENSORY STIMULATION DELIVERED TO A USER USING NEURAL NETWORKS

This application claims the benefit of U.S. Provisional Applications 62/669,526, filed on 2018 May 10 and 62/691,269, filed on 28 Jun. 2018. These applications are hereby incorporated by reference herein.

BACKGROUND

1. Field

The present disclosure pertains to a system and method for enhancing sensory stimulation delivered to a user using neural networks.

2. Description of the Related Art

Systems for monitoring sleep and delivering sensory stimulation to users during sleep are known. Electroencephalogram (EEG) sensor based sleep monitoring and sensory stimulation systems are known. These systems are state-based, meaning stimulation is delivered responsive to EEG parameters breaching sleep stage stimulation delivery thresholds. These state-based determinations do not account for changes in user characteristics, such as age and other demographic parameters. As a result, users may receive less stimulation than they might otherwise, or the stimulation timing may not adequately correspond to their individual sleeping patterns. Thus, there is a need for a system that is able to generate accurate information about a sleeping subject relative to prior art systems to enhance delivery of sensory stimulation during sleep sessions.

SUMMARY

Accordingly, one or more aspects of the present disclosure relate to a system configured to deliver sensory stimulation to a user during a sleep session. The system comprises one or more sensors, one or more sensory stimulators, one or more hardware processors, and/or other components. The one or more sensors are configured to generate output signals conveying information related to brain activity of the user during the sleep session. The one or more sensory stimulators are configured to provide sensory stimulation to the user during the sleep session. The one or more hardware processors are coupled to the one or more sensors and the one or more sensory stimulators. The one or more hardware processors configured by machine-readable instructions. The one or more hardware processors are configured to obtain historical sleep depth information for a population of users. The historical sleep depth information is related to brain activity of the population of users that indicates sleep depth over time during sleep sessions of the population of users. The one or more hardware processors are configured to cause a neural network to be trained based on the historical sleep depth information by providing the historical sleep depth information as input to the neural network. The one or more hardware processors are configured to cause, based on the output signals, the trained neural network to predict future times during the sleep session at which the user will be in a deep sleep stage. The trained neural network comprises an input layer, an output layer, and one or more intermediate layers between the input layer and the output layer. The one or more hardware processors are configured to determine, with respect to each of the future times, one or more values generated by the one or more intermediate layers of the trained neural network. The one or more hardware processors are configured to cause the one or more sensory stimulators to provide the sensory stimulation to the user at the future times, and to modulate a timing and/or intensity of the sensory stimulation during the sleep session based on the one or more values of the one or more intermediate layers.

Another aspect of the present disclosure relates to a method for delivering sensory stimulation to a user during a sleep session with a delivery system. The system comprises one or more sensors, one or more sensory stimulators, one or more hardware processors coupled to the one or more sensors and the one or more sensory stimulators, and/or other components. The one or more hardware processors are configured by machine-readable instructions. The method comprises generating, with the one or more sensors, output signals conveying information related to brain activity of the user during the sleep session. The method comprises providing, with the one or more sensory stimulators, sensory stimulation to the user during the sleep session. The method comprises obtaining, with the one or more hardware processors, historical sleep depth information for a population of users. The historical sleep depth information is related to brain activity of the population of users that indicates sleep depth over time during sleep sessions of the population of users. The method comprises causing, with the one or more hardware processors, a neural network to be trained based on the historical sleep depth information by providing the historical sleep depth information as input to the neural network. The method comprises causing, with the one or more hardware processors, based on the output signals, the trained neural network to predict future times during the sleep session at which the user will be in a deep sleep stage. The trained neural network comprises an input layer, an output layer, and one or more intermediate layers between the input layer and the output layer. The method comprises determining, with the one or more hardware processors, with respect to each of the future times, one or more values generated by the one or more intermediate layers of the trained neural network. The method comprises causing, with the one or more hardware processors, the one or more sensory stimulators to provide the sensory stimulation to the user at the future times, and to modulate a timing and/or intensity of the sensory stimulation during the sleep session based on the one or more values of the one or more intermediate layers.

Yet another aspect of the present disclosure relates to a system for a system for delivering sensory stimulation to a user during a sleep session. The system comprises means for generating output signals conveying information related to brain activity of the user during the sleep session. The system comprise means for providing sensory stimulation to the user during the sleep session. The system comprises means for obtaining historical sleep depth information for a population of users. The historical sleep depth information is related to brain activity of the population of users that indicates sleep depth over time during sleep sessions of the population of users. The system comprises means for causing a neural network to be trained based on the historical sleep depth information by providing the historical sleep depth information as input to the neural network. The system comprises means for causing, based on the output signals, the trained neural network to predict future times during the sleep session at which the user will be in a deep sleep stage. The trained neural network comprises an input layer, an output layer, and one or more intermediate layers between the input layer and the output layer. The system comprises means for determining, with respect to each of the future times, one or more values generated by the one or more intermediate layers of the trained neural network. The system comprises means for causing the one or more sensory stimulators to provide the sensory stimulation to the user at the future times, and to modulate a timing and/or intensity of the sensory stimulation during the sleep session based on the one or more values of the one or more intermediate layers.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
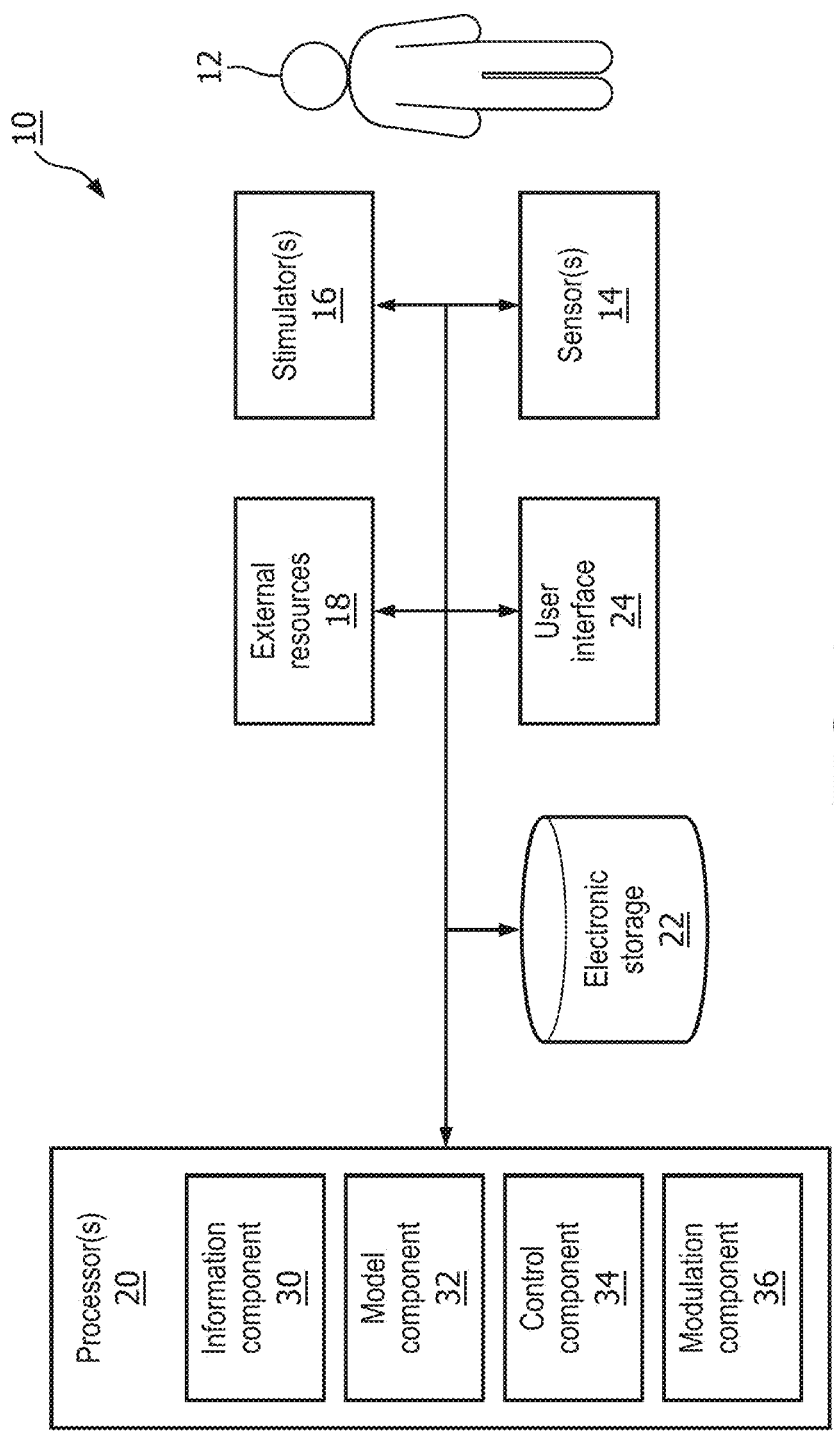
FIG. 1 is a schematic illustration of a system configured to deliver sensory stimulation to a user during a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to deliver sensory stimulation to a user 12 during a sleep session. System 10 is configured to facilitate delivery of sensory stimulation to user 12 to enhance the restorative effects of sleep in user 12 and/or for other purposes. System 10 is configured such that sensory stimulation including auditory and/or other stimulation delivered during sleep enhances slow waves in user 12 without causing arousals, which brings cognitive benefits and enhancement of sleep restoration, for example. As described herein, in some embodiments, system 10 is configured to determine periods of deep sleep during a sleep session (e.g., based on output from a neural network and/or other information). In some embodiments, based on such determinations, system 10 is configured to modulate sensory (e.g., auditory) stimulation delivered to user 12 to enhance sleep slow waves without causing arousals. In some embodiments, periods of deep sleep may be determined in real-time and/or near real-time during a sleep session of user 12.

Automatic sleep staging in real-time or near real-time based on sensor output signals is often challenging because sleep therapy systems have only limited control of the therapy conditions (e.g., a sleep therapy system typically does not control the background noise, the lighting, or other features of the sleeping environment in a user's home) where the therapy is delivered. To ensure fast processing of sensor output signals to enable real-time or near real-time sleep therapy, prior art systems typically rely on state based algorithms of limited complexity. For example, these systems typically place thresholds on common parameters determined from sensor output signals (e.g., thresholds of 0.5-4 Hz on a delta power band of an electroencephalogram (EEG), 8-13 Hz on an alpha band, 15-30 Hz on a beta band, etc.), and use these thresholds to determine sleep stages to time delivery of sensory stimulation. This makes it difficult to reliably detect specific sleep stages, especially for users from different demographic groups. As one example, the sleep architecture and EEG patterns are different for users of different ages. Often these differences cause prior art systems to deliver less (or more) stimulation than they might otherwise if the methods they used to detect sleep stages were enhanced.

System 10 addresses the limitations of prior art systems by leveraging machine-learning models (e.g., deep neural networks as described below) for automatic, real-time or near real-time, sensor output signal based sleep staging. System 10 uses the overall output from the machine-learning models for sleep staging, as well as intermediate values output from the models to modulate sensory stimulation provided by system 10. In some embodiments, system 10 includes one or more of a sensor 14, a sensory stimulator 16, external resources 18, a processor 20, electronic storage 22, a user interface 24, and/or other components.

Sensor 14 is configured to generate output signals conveying information related to brain activity and/or other activity in user 12. In some embodiments, sensor 14 is configured to generate output signals conveying information related to brain activity such as slow wave activity in user 12. In some embodiments, the information related to brain activity and/or other activity in user 12 is the information related to slow wave activity. In some embodiments, sensor 14 is configured to generate output signals conveying information related to stimulation provided to user 12 during sleep sessions. In some embodiments, the information in the output signals from sensor 14 is used to control sensory stimulator 16 to provide sensory stimulation to user 12 (as described below).

Sensor 14 may comprise one or more sensors that generate output signals that convey information related to brain activity in user 12 directly. For example, sensor 14 may include electroencephalogram (EEG) electrodes configured to detect electrical activity along the scalp of user 12 resulting from current flows within the brain of user 12. Sensor 18 may comprise one or more sensors that generate output signals conveying information related to brain activity of user 12 indirectly. For example, one or more sensors 14 may comprise a heart rate sensor that generates an output based on a heart rate of user 12 (e.g., sensor 14 may be a heart rate sensor than can be located on the chest of user 12, and/or be configured as a bracelet on a wrist of user 12, and/or be located on another limb of user 12), movement of user 12 (e.g., sensor 14 may comprise an accelerometer that can be carried on a wearable, such as a bracelet around the wrist and/or ankle of user 12 such that sleep may be analyzed using actigraphy signals), respiration of user 12, and/or other characteristics of user 12.

In some embodiments, sensor 14 may comprise one or more of EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) the stimulation provided to user 12, and/or other sensors. Although sensor 14 is illustrated at a single location near user 12, this is not intended to be limiting. Sensor 14 may include sensors disposed in a plurality of locations, such as for example, within (or in communication with) sensory stimulator 16, coupled (in a removable manner) with clothing of user 12, worn by user 12 (e.g., as a headband, wristband, etc.), positioned to point at user 12 while user 12 sleeps (e.g., a camera that conveys output signals related to movement of user 12), coupled with a bed and/or other furniture where user 12 is sleeping, and/or in other locations.

In FIG. 1, sensor 18, sensory stimulator 16, processor 20, electronic storage 22, and user interface 24 are shown as separate entities. This is not intended to be limiting. Some and/or all of the components of system 10 and/or other components may be grouped into one or more singular devices. For example, these and/or other components may be included in a headset and/or other garments worn by user 12. Such a headset may include, for example, sensing electrodes, a reference electrode, one or more devices associated with an EEG, means to deliver auditory stimulation (e.g., a wired and/or wireless audio device and/or other devices), and one or more audio speakers. In this example, the audio speakers may be located in and/or near the ears of user 12 and/or in other locations. The reference electrode may be located behind the ear of user, and/or in other locations. In this example, the sensing electrodes may be configured to generate output signals conveying information related to brain activity of user 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to user 12 via the wireless audio device and/or speakers. In this example, the sensing electrodes, the reference electrode, and the EEG devices may be represented, for example, by sensor 14 in FIG. 1. The wireless audio device and the speakers may be represented, for example, by sensory stimulator 16 shown in FIG. 1. In this example, a computing device may include processor 20, electronic storage 22, user interface 24, and/or other components of system 10 shown in FIG. 1.

Stimulator 16 is configured to provide sensory stimulation to user 12. Sensory stimulator 16 is configured to provide auditory, visual, somatosensory, electric, magnetic, and/or sensory stimulation to user 12 prior to a sleep session, during a sleep session, and/or at other times. In some embodiments, a sleep session may comprise any period of time when user 12 is sleeping and/or attempting to sleep. Sleep sessions may include nights of sleep, naps, and/or other sleeps sessions. For example, sensory stimulator 16 may be configured to provide stimuli to user 12 during a sleep session to facilitate a transition to a deeper stage of sleep, a lighter stage of sleep, maintain sleep in a specific stage, enhance the restorative effects of sleep, and/or for other purposes. In some embodiments, sensory stimulator 16 may be configured such that facilitating a transition between deeper sleep stages and lighter sleep stages includes decreasing sleep slow waves in user 12, and facilitating a transition between lighter sleep stages and deeper sleep stages includes increasing sleep slow waves.

Sensory stimulator 16 is configured to facilitate transitions between sleep stages, maintain sleep in a specific stage, and/or enhance the restorative effects of sleep through non-invasive brain stimulation and/or other methods. Sensory stimulator 16 may be configured to facilitate transitions between sleep stages, maintain sleep in a specific stage, and/or enhance the restorative effects of sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, acoustic tones may be provided to user 12 to enhance the restorative effects of sleep in user 12. The acoustic tones may include one or more series of tones of a determined length separated from each other by an inter-tone interval. The volume (e.g., the intensity) of individual tones may be modulated based on sleep depth and other factors (as described herein) such that loud tones are played during deeper sleep and soft tones are played during lighter sleep. The length of individual tones (e.g., the timing) and/or the inter tone interval (e.g., the timing) may also be adjusted depending on whether user 12 is in deeper or lighter sleep. This example is not intended to be limiting. Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to user 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. For example, external resources 18 may include sources of historical sleep depth information for a population of users, and/or other information. The historical sleep depth information for the population of users may be related to brain activity of the population of users that indicates sleep depth over time during sleep sessions of the population of users. In some embodiments, the historical sleep depth information for the population of users may be related to a user population in a given geographical area; demographic information related to gender, ethnicity, age, a general health level, and/or other demographic information; physiological information (e.g., weight, blood pressure, pulse, etc.) about the population of users, and/or other information. In some embodiments, this information may indicate whether an individual user in the population of user is demographically, physiologically, and/or otherwise similar to user 12.

In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 18 may be provided by resources included in system 10. External resources 18 may be configured to communicate with processor 20, user interface 24, sensor 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a modulation component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to determine one or more brain activity parameters of user 12. The brain activity parameters are determined based on the output signals from sensor 14 and/or other information. The brain activity parameters indicate depth of sleep in the user. In some embodiments, the information in the output signals related to brain activity indicates sleep depth over time. In some embodiments, the information indicating sleep depth over time is or includes information related to slow wave activity in user 12. In some embodiments, the slow wave activity of user 12 may be indicative of sleep stages of user 12. The sleep stages of user 12 may be associated with rapid eye movement (REM) sleep, non-rapid eye movement (NREM) sleep, and/or other sleep. The sleep stages of the population of users may be one or more of NREM stage N1, stage N2, or stage N3, REM sleep, and/or other sleep stages. In some embodiments, the sleep stages of user 12 may be one or more of stage S1, S2, S3, or S4. In some embodiments, NREM stage 2 and/or 3 (and/or S3 and/or S4) may be slow wave (e.g., deep) sleep. In some embodiments, the information related to brain activity that indicates sleep depth over time is and/or is related to one or more additional brain activity parameters.

In some embodiments, the information related to brain activity that indicates sleep depth over time is and/or includes EEG information generated during sleep sessions of the population of users. In some embodiments, brain activity parameters may be determined based on the EEG information. In some embodiments, the brain activity parameters may be determined by information component 30 and/or other components of system 10. In some embodiments, the brain activity parameters may be previously determined and be part of the historical sleep depth information obtained from external resources 18. In some embodiments, the one or more brain activity parameters are and/or are related to a frequency, amplitude, phase, presence of specific sleep patterns such as spindles, K-complexes, or sleep slow waves, alpha waves, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate sleep stages that correspond to the REM and/or NREM sleep stages described above. For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 4 Hz), also known as sleep slow waves, with peak-to-peak amplitudes greater than about 75 uV for sleep stage N3; presence of light sleep and/or arousals, and/or other characteristics. In some embodiments, light sleep may be characterized by the fact that the alpha activity (e.g., EEG power in the 8-12 Hz band) is no longer present and slow waves are not present. In some embodiments, slow wave activity is a continuous value (e.g., EEG power in the 0.4 to 4 Hz band), which is positive. In some embodiments, an absence of slow waves is indicative of light sleep. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, EEG power in the delta band and SWA are the same when considering sleep EEG. In some embodiments, the information related to brain activity that indicates sleep depth over time indicates changes in an EEG delta power over time, a quantity of micro arousals in the population of users, other EEG power levels, and/or other parameters.

Information component 30 is configured to obtain historical sleep depth information. In some embodiments, the historical sleep depth information is for a population of users. In some embodiments, the historical sleep depth information is for user 12. The historical sleep depth information is related to brain activity of the population of users and/or user 12 that indicates sleep depth over time during previous sleep sessions of the population of users and/or user 12. The historical sleep depth information is related to sleep stages and/or other brain activity parameters of the population of users and/or user 12 during corresponding sleep sessions, and/or other information. In some embodiments, information component 30 is configured to obtain the historical sleep depth information electronically from external resources 18, electronic storage 22, and/or other sources of information. In some embodiments, obtaining the historical sleep depth information electronically from external resources 18, electronic storage 22, and/or other sources of information comprises querying one more databases and/or servers; uploading information and/or downloading information, facilitating user input (e.g., criteria used to define a target patient population input via user interface 24), sending and/or receiving emails, sending and/or receiving text messages, and/or sending and/or receiving other communications, and/or other obtaining operations. In some embodiments, information component 30 is configured to aggregate information from various sources (e.g., one or more of the external resources 18 described above, electronic storage 22, etc.), arrange the information in one or more electronic databases (e.g., electronic storage 22, and/or other electronic databases), normalize the information based on one or more features of the historical sleep depth information (e.g., length of sleep sessions, number of sleep sessions, etc.) and/or perform other operations.

Model component 32 is configured to cause a machine-learning model to be trained using the historical sleep depth information. In some embodiments, the machine-learning model is trained based on the historical sleep depth information by providing the historical sleep depth information as input to the machine-learning model. In some embodiments, the machine-learning model may be and/or include mathematical equations, algorithms, plots, charts, networks (e.g., neural networks), and/or other tools and machine-learning model components. For example, the machine-learning model may be and/or include one or more neural networks having an input layer, an output layer, and one or more intermediate or hidden layers. In some embodiments, the one or more neural networks may be and/or include deep neural networks (e.g., neural networks that have one or more intermediate or hidden layers between the input and output layers).

As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function that combines the values of all its inputs together. In some embodiments, each connection (or the neural unit itself) may have a threshold function such that a signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

As described above, the trained neural network may comprise one or more intermediate or hidden layers. The intermediate layers of the trained neural network include one or more convolutional layers, one or more recurrent layers, and/or other layers of the trained neural network. Individual intermediate layers receive information from another layer as input and generate corresponding outputs. The predicted sleep stages and/or future times of deep sleep stages are generated based on the information in the output signals from sensor 14 as processed by the layers of the neural network.

Model component 32 is configured such that the trained neural network is caused to indicate predicted sleep stages for user 12. In some embodiments, this may be and/or include causing the trained neural network to predict future times during the sleep session at which user 12 will be in a deep sleep stage. The predicted sleep stages and/or timing indicates whether the user is in deep sleep for stimulation and/or other information. The trained neural network is caused to indicate predicted sleep stages and/or future times and/or timing of the deep sleep stages for the user based on the output signals (e.g., using the information in the output signals as input for the model) and/or other information. The trained neural network is configured to indicate sleep stages predicted to occur at future times for user 12 during the sleep session. In some embodiments, model component 32 is configured to provide the information in the output signals to the neural network in temporal sets that correspond to individual periods of time during the sleep session. In some embodiments, model component 32 is configured to cause the trained neural network to output the predicted sleep stages and/or predicted times of deep sleep stages for user 12 during the sleep session based on the temporal sets of information. (The functionality of model component 32 is further discussed below relative to FIG. 2-9.)

Control component 34 is configured to control stimulator 16 to provide stimulation to user 12 during sleep and/or at other times. Control component 34 is configured to cause sensory stimulator 16 to provide sensory stimulation to user 12 based on a predicted sleep stage (e.g., the output from model component 32) and/or future times at which user 12 will be in a deep sleep stage, and/or other information. Control component 34 is configured to cause sensory stimulator 16 to provide the sensory stimulation to user 12 based on the predicted sleep stage and/or future times, and/or other information over time during the sleep session. Control component 34 is configured to cause sensory stimulator 16 to provide sensory stimulation to user 12 responsive to user 12 being in, or likely being in, deep sleep for stimulation (e.g., deep (N3) sleep).

In some embodiments, stimulators 16 are controlled by control component 34 to enhance sleep slow waves through (e.g. peripheral auditory, magnetic, electrical, and/or other) stimulation delivered in NREM sleep (as described herein). In some embodiments, control component 34 (and/or one or more of the other processor components described herein) performs one or more operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties. (The functionality of control component 34 is further discussed below relative to FIG. 2-9.)

Modulation component 36 is configured to cause sensory stimulator 16 to modulate a timing and/or intensity of the sensory stimulation. Modulation component 36 is configured to cause sensory stimulator 16 to modulate the timing and/or intensity of the sensory stimulation based on the brain activity parameters, values output from the intermediate layers of the trained neural network, and/or other information. As an example, sensory stimulator 16 is caused to modulate the timing and/or intensity of the sensory stimulation based on the brain activity parameters, the values output from the convolutional layers, the values output from the recurrent layers, and/or other information. For example, modulation component 36 may be configured such that sensory stimulation is delivered with an intensity that is proportional to a predicted probability value (e.g., an output from an intermediate layer of a neural network) of a particular sleep stage (e.g., N3). In this example, the higher the probability of N3 sleep, the more intense the stimulation. (The functionality of modulation component 36 is further discussed below relative to FIG. 2-9.)

Figure 2:
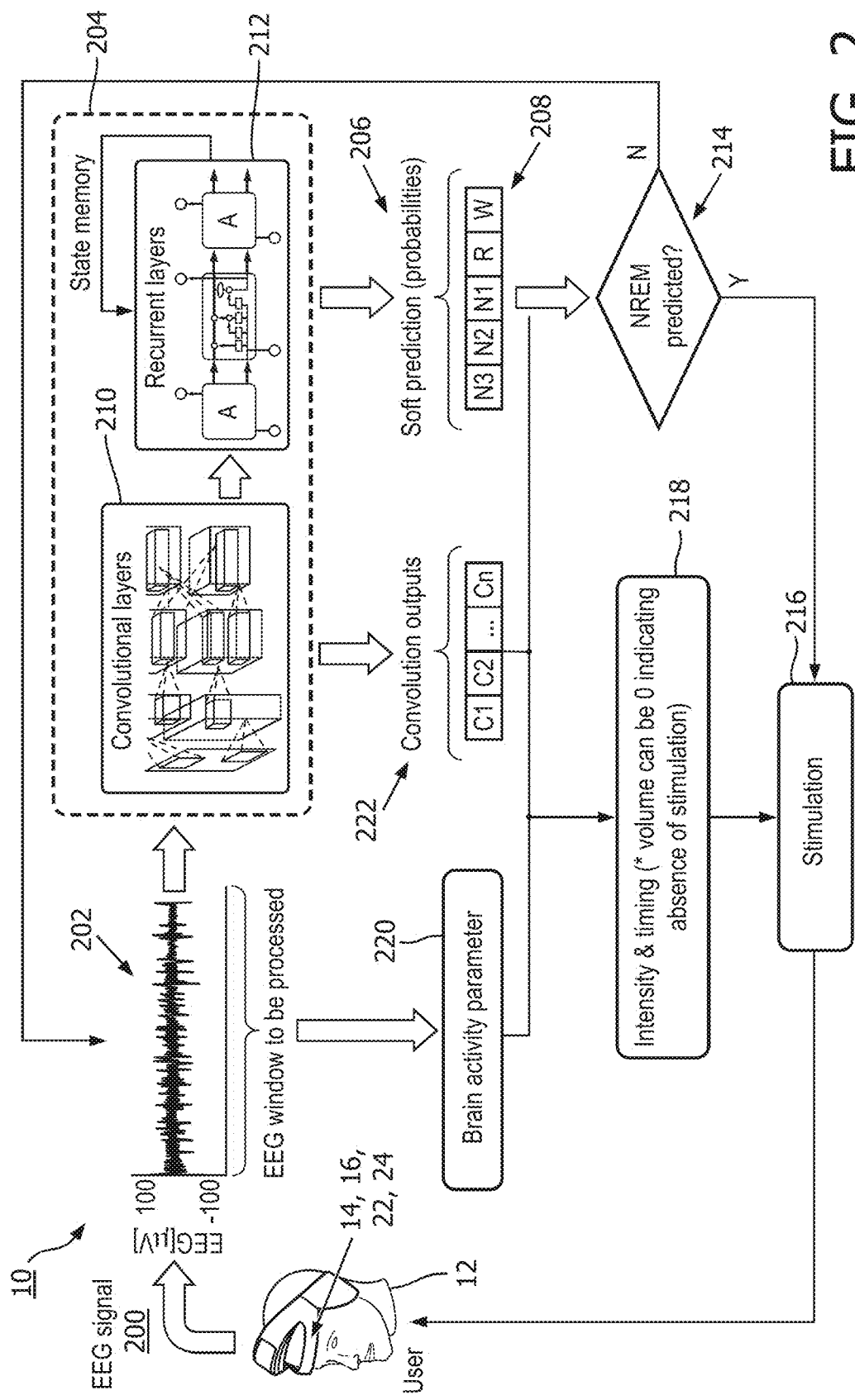
FIG. 2 illustrates several of the operations performed by the system, in accordance with one or more embodiments.

By way of a non-limiting example, FIG. 2 illustrates several of the operations performed by system 10 and described above. In the example shown in FIG. 2, an EEG signal 200 is processed and/or otherwise provided (e.g., by information component 30 and model component 32 shown in FIG. 1) to a deep neural network 204 in temporal windows 202. Deep neural network 204 predicts 206 future sleep stages 208 and/or future times where a user will be in deep sleep (illustrated as N3, N2, N1, R (REM), and W (wakefulness)) based on the information in temporal windows 202. In some embodiments, the prediction window is about tens of seconds to a few minutes, for example. Predicting future sleep stages and/or timing of deep sleep stages facilitates provision of sensory stimulation to enhance slow wave sleep because it enables system 10 to either withhold stimulation (if lighter sleep stages are predicted) or prepare for stimulation with optimized timing and intensity when deeper (e.g., NREM) sleep is predicted. The architecture of deep neural network 204 includes convolutional layers 210 (which can be thought of as filters) and recurrent layers 212 (which, as just one example, may be implemented as longshort term memory elements) that endow network 204 with memory to be able to use past predictions to refine prediction accuracy.

As shown in FIG. 2, responsive to sleep stage predictions 208 indicating NREM sleep is predicted (e.g., deep sleep for the provision of sensory stimulation) 214, stimulation 216 is provided to user 12 (e.g., from sensory stimulator 16 controlled by control component 34 shown in FIG. 1). The intensity and/or timing of stimulation 216 is modulated 218 (e.g., by modulation module 36) based on brain activity parameters 220 (e.g., determined by information component 30 shown in FIG. 1), outputs 222 from the convolutional layers of the deep neural network (illustrated as constants $C_1, C_2, \ldots, C_n$), and predicted sleep stages 208. As described above, in some embodiments, the sensory stimulation comprises audible tones. In these embodiments, sensory stimulators 16 may modulate the timing and/or intensity of the sensory stimulation by decreasing an inter tone interval and/or increasing a tone volume responsive to the brain activity parameters and/or the output from the intermediate layers (e.g., convolutional layers 210 and/or recurrent layers 212) indicating the user is in deep and/or deep sleep for stimulation.

Figure 3:
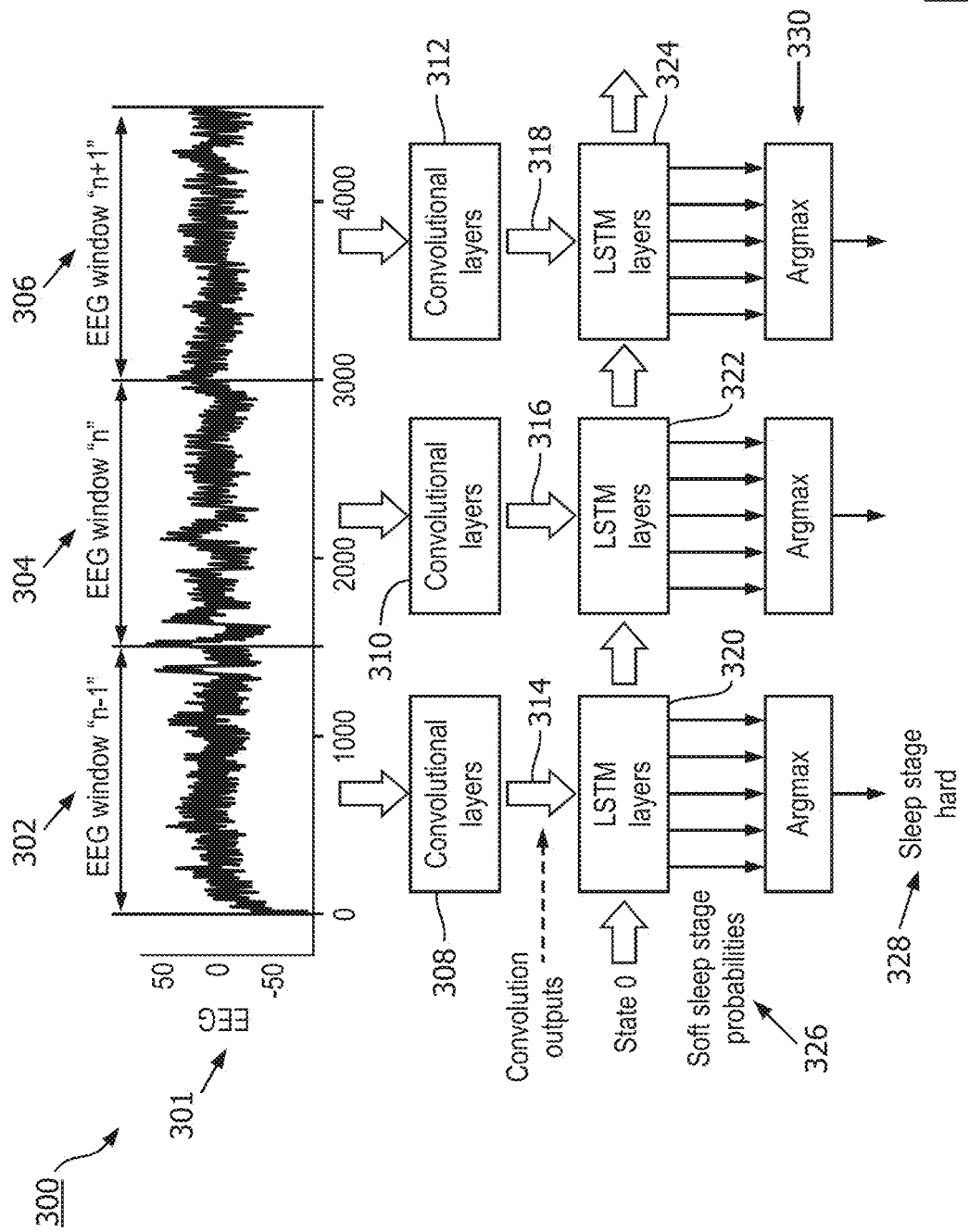
FIG. 3 illustrates example architecture of a deep neural network that is part of the system, in accordance with one or more embodiments.

FIG. 3 illustrates example architecture 300 of a deep neural network (e.g., deep neural network 204 shown in FIG. 2) that is part of system 10 (FIGS. 1 and 2). FIG. 3 illustrates deep neural network architecture 300 for three (unrolled) EEG 301 windows 302, 304, and 306. Architecture 300 includes convolutional layers 308, 310, and 312, and recurrent layers 320, 322, and 324. As described above, convolutional layers 308, 310, and 312 can be thought of as filters and produce convolution outputs 314, 316, and 318 that are fed to recurrent layers 320, 322, 324 (LSTM (long short term memory) layers in this example). The output of architecture 300 for individual windows 302, 304, 306 that are processed are a set of prediction probabilities for individual sleep stages, which are termed "soft output(s)" 326.

"Hard" predictions 328 are determined by architecture 300 (model component 32 shown in FIG. 1) by predicting 330 a sleep stage associated with a "soft" output with the highest value (e.g., as described below). The terms "soft" and "hard" are not intended to be limiting but may be helpful to use to describe the operations performed by the system. For example, the term "soft output" may be used, because at this stage, any decision is possible. Indeed, the final decision could depend on post-processing of the soft outputs, for example. "Argmax" in FIG. 3 is an operator that indicates the sleep stage associated with the highest "soft output" (e.g., the highest probability).

For example, a useful property of neural networks is that they can produce probabilities associated with pre-defined sleep stages (e.g. Wake, REM, N1, N2, N3 sleep). Model component 32 (FIG. 1) is configured such that the set of probabilities constitute a so-called soft decision vector, which may be translated into a hard decision by determining which sleep stage is associated with a highest probability value (in a continuum of possible values) relative to other sleep stages. These soft decisions make it possible for system 10 to consider different possible sleep states on a continuum rather than being forced to decide which discrete sleep stage "bucket" particular EEG information fits into (as in prior art systems).

Returning to FIG. 1, model component 32 is configured such that both the values output from convolutional layers, and the soft decision value outputs, are vectors comprising continuous values as opposed to discrete values such as sleep stages. Consequently, convolutional and recurrent (soft-decision) value outputs are available to be used by system 10 to modulate the volume of the stimulation when the deep neural network predicts occurrences of NREM sleep, for example. In addition, as described herein, parameters determined (e.g., by information component 30 shown in FIG. 1) based on the raw EEG signal can be used to modulate stimulation settings. As described above, these parameters include sleep depth parameters (e.g., a ratio between the EEG power in the delta band and the EEG power in the beta band), the density of detected slow-waves per unit of time, the power in the delta band, and/or other parameters.

As described above, modulation component 36 is configured to cause sensory stimulator 16 to modulate a timing and/or intensity of the sensory stimulation. Modulation component 36 is configured to cause sensory stimulator to modulate the timing and/or intensity of the sensory stimulation based on the one or more brain activity parameters, values output from the convolutional and/or recurrent layers of the trained neural network, and/or other information. As an example, the volume of auditory stimulation provided to user 12 may be adjusted and/or otherwise controlled (e.g., modulated) based on value outputs from the deep neural network such as convolutional layer value outputs and recurrent layer value outputs (e.g., sleep stage (soft) prediction probabilities).

Figure 4:
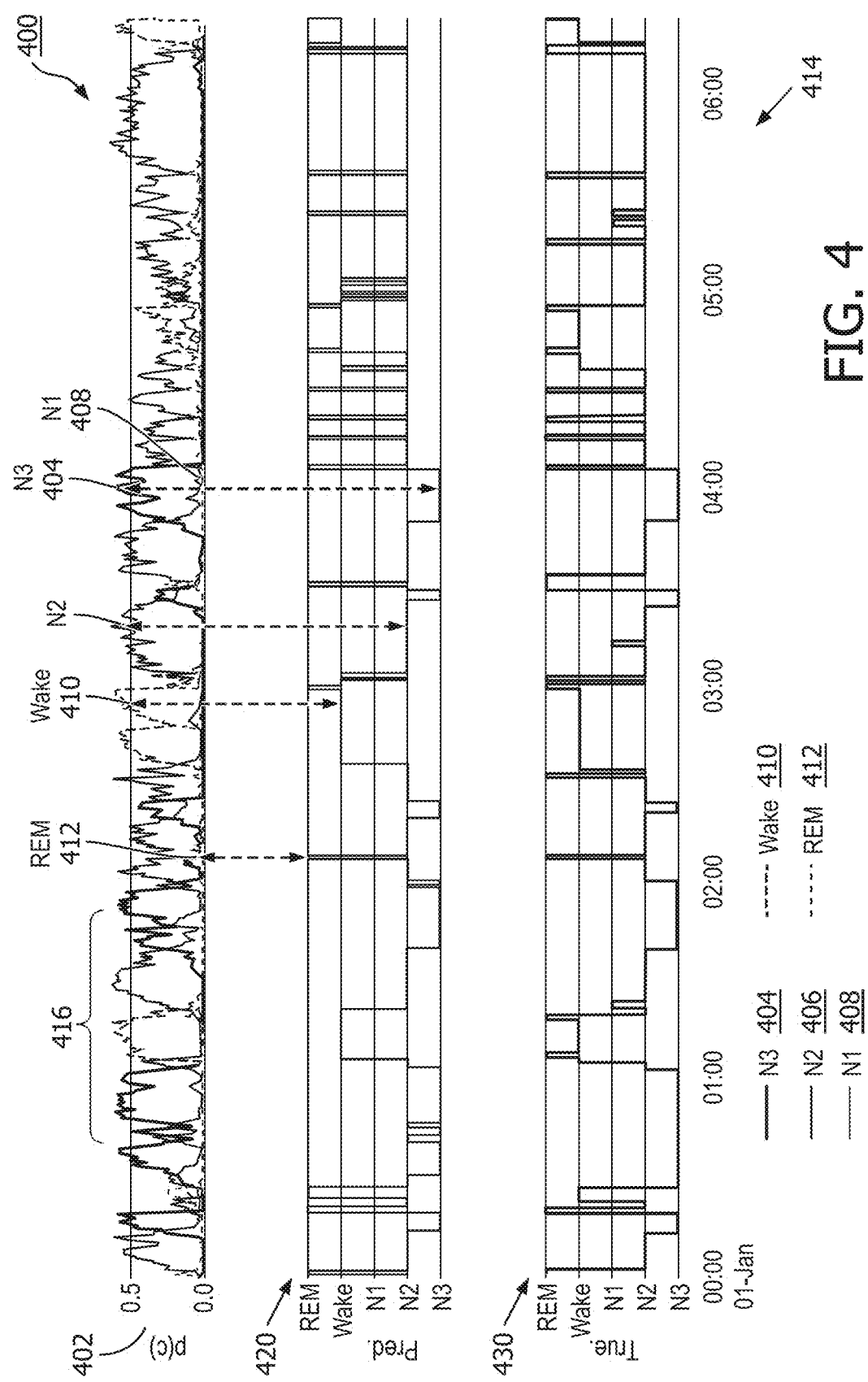
FIG. 4 illustrates an example of a continuum of sleep stage probability values for sleep stages N3, N2, N1, wake, and REM across moments in time for a sleep session, in accordance with one or more embodiments.

FIG. 4 illustrates an example of a continuum 400 of sleep stage probability values (p(c)) 402 for sleep stages N3 404, N2 406, N1 408, wake 410, and REM 412 across future moments in time 414 for the sleep session. FIG. 4 also illustrates a hard output 420, which is the sleep stage associated with the highest prediction probability value 402 (on a zero to one scale in this example) across future moments in time 414 for the sleep session. Finally, FIG. 4 illustrates a manually annotated hypnogram 430 (e.g., manually annotated by an expert sleep technician) for the sleep session for reference. In contrast to a system that predicts a single discrete sleep stage for each moment in time during a sleep session, model component 32 (FIG. 1) is configured such that the sleep stage prediction probabilities for individual sleep stages behave as waveforms 416, varying across a continuum of values between zero and one (in this example) over time. In addition to being used by model component 32 to generate hard outputs (e.g., predicted sleep stages for user 12), the values of these waveforms at various time points 414 can be used by modulation component 36 (FIG. 1) along with convolutional layer outputs, parameters determined by information component 30 (FIG. 1) and/or other information to modulate auditory stimulation during detected N3 sleep.

Figures 5A, 5B:
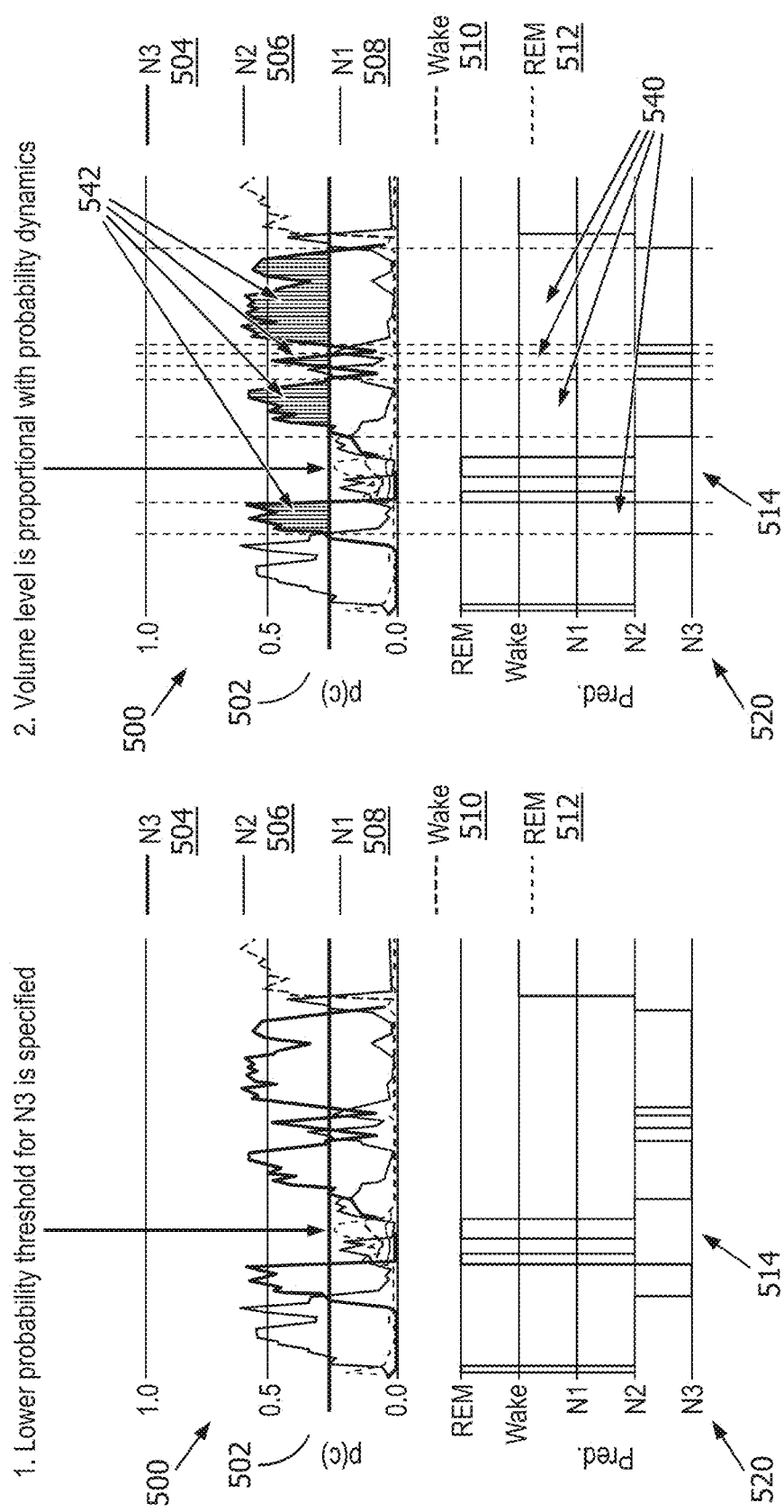
FIGS. 5A and 5B illustrate an example where a prediction probability value associated with N3 sleep is used to determine when to provide stimulation to the user, and to determine the volume of the stimulation, in accordance with one or more embodiments.

FIGS. 5A and 5B illustrate an example where the prediction probability value associated with N3 sleep is used (e.g., by model component 32 and control component 34 shown in FIG. 1) to determine when to provide stimulation to user 12 (FIG. 1), and (by modulation component 36) to modulate (e.g., determine the volume of in this example) the stimulation. FIG. 5A illustrates a continuum 500 of sleep stage probability values (p(c)) 502 for sleep stages N3 504, N2 506, N1 508, wake 510, and REM 512 across future moments in time 514 for a sleep session. FIG. 5A also illustrates a hard output sleep stage prediction 520, which is the sleep stage associated with the highest prediction probability value 502 (on the zero to one scale in this example). FIG. 5B repeats the illustrations of sleep stage probability continuum 500 and hard output sleep stage prediction 520, but also illustrates how, for predicted periods of N3 sleep 540, tones are delivered with a volume that is proportional to the predicted N3 probability value. The regions of the N3 prediction probability continuum 500 where stimulation is delivered are shaded 542. Modulation component 36 (FIG. 1) is configured such that the volume (e.g., intensity) of the tones (e.g., sensory stimulation) is proportional to the probability value of N3 sleep. Essentially, the higher the N3 prediction probability value, the louder the volume of the stimulation. For the system to detect N3 sleep, the probability of N3 should be the highest among all the other stages. By way of a non-limiting example, the N3 threshold referred to here is used for stimulation. Once N3 sleep is detected (i.e. the probability of N3 was the highest), stimulation is delivered if the probability of N3 exceeds a threshold. To set the threshold, the distribution of N3 probability once N3 is detected is used (0.65 in this example—this ensures 50% of detected N3 will receive stimulation). The volume is proportional to the N3 probability (once the threshold has been exceeded)

Figure 6:
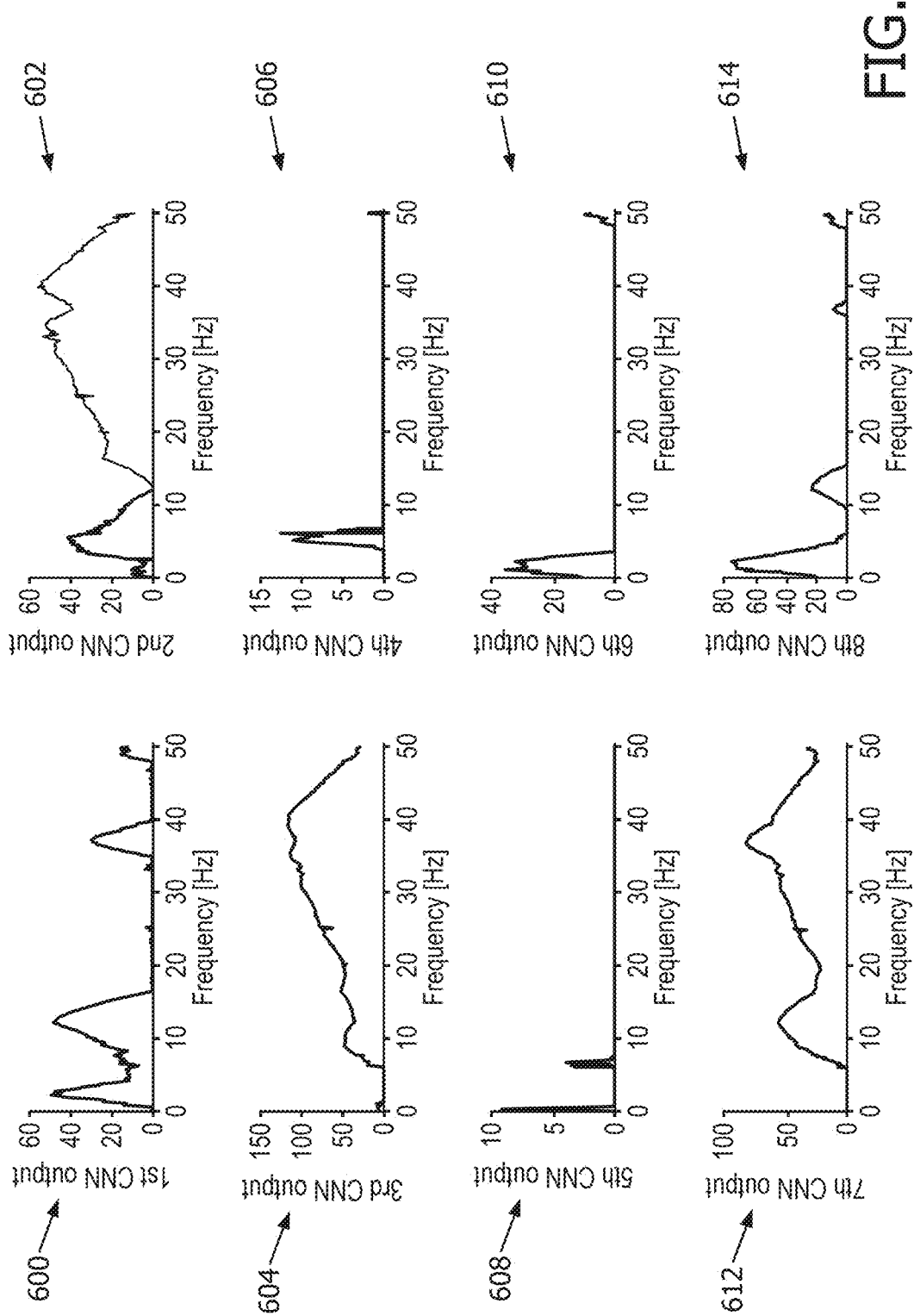
FIG. 6 illustrates convolutional layer value outputs from a deep neural network trained to predict sleep stages as described herein, in accordance with one or more embodiments.

As described above, modulation component 36 (FIG. 1) is configured to utilize neural network convolutional layer outputs to modulate stimulation delivered to user 12. In some embodiments, the neural network convolutional outputs may be used instead of the probability values and/or other parameters (e.g., determined directly from the EEG) described above to modulate the stimulation. In some embodiments, the neural network convolutional outputs may be used in addition to the probability values and/or other parameters (e.g., determined directly from the EEG) described above to modulate the stimulation. The convolutional layer outputs may be thought of as outputs from a filter bank. By way of a non-limiting example, convolutional layer outputs from a deep neural network trained to predict sleep stages as described herein are shown in FIG. 6. Such convolutional layer outputs may comprise outputs in the frequency domain and/or other outputs. FIG. 6 shows eight total outputs 600-614, for example. These outputs were generated, using as EEG input, 30-second long, 200-microvolt peak-to-peak, co-sinusoidal signals at single frequencies ranging from 0.1 to 50 Hz (by steps of 0.1 Hz). The profile of the frequency domain convolutional outputs reveals clear sleep related relevance of the outputs 600-614. For example, 4th to 6th outputs 606-610 show narrow band outputs, where the 4th output 606 responds to activity in the theta band (4 to 7 Hz), the 5th output 608 responds to infra-slow (<0.6 Hz) oscillations and a narrow sub-theta band (6 to 7 Hz), and the 6th output 610 responds to delta band activity. The 3rd and 7th outputs 604 and 612 respond to activities in any band but the delta band. The 1st and 8th outputs 600 and 614 respond to multimodal activities in the delta band, spindle (sigma 11 to 16 Hz) activity, and a narrow gamma activity (35 to 40 Hz) range.

In some embodiments, modulation component 36 (FIG. 1) is configured such that individual convolutional layer outputs (e.g., the outputs shown in FIG. 6) are used as a basis for modulating the timing and intensity of the stimulation. In some embodiments, modulation component 36 is configured such that a plurality of convolutional layer outputs facilitate modulating the timing and intensity (e.g., volume) of the stimulation. In some embodiments, the output from the one or more convolutional layers comprises two or more individual outputs from two or more corresponding convolutional layers. In some embodiments, modulation component 36 is configured to determine a ratio of output from one convolutional layer to output from another convolutional layer. In some embodiments, modulation component 36 is configured to cause the one or more sensory stimulators to modulate the timing and/or intensity of the sensory stimulation based on the ratio.

Figure 7:
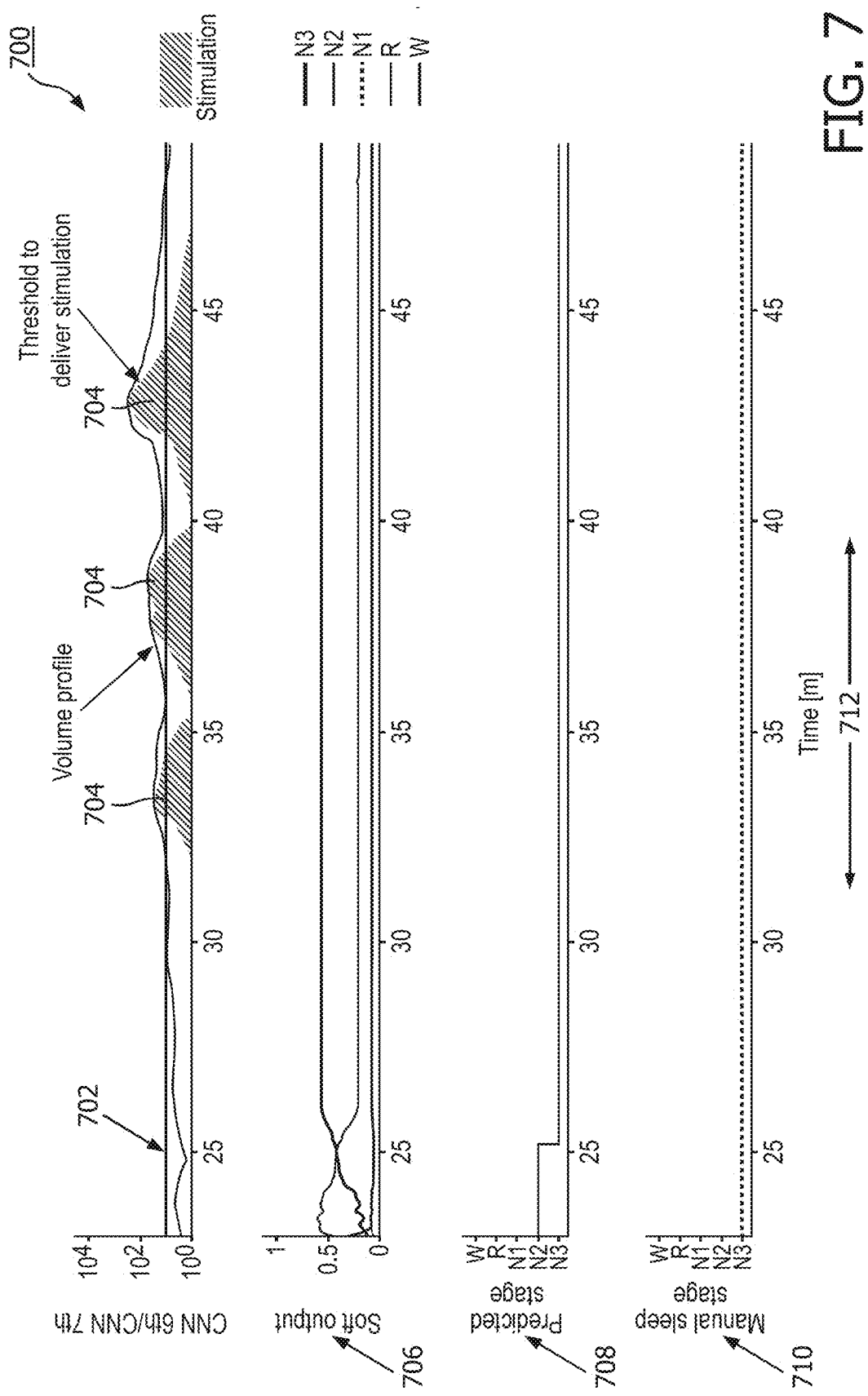
FIG. 7 illustrates a ratio between convolutional layer value outputs used to modulate stimulation provided to a user, in accordance with one or more embodiments.

For example, depth of sleep may be estimated by taking the ratio between the EEG power in a low frequency band and the EEG power in a high frequency band. Thus, the ratio between the 6th and 7th outputs 610 and 612 during detected NREM sleep may be, for example, an appropriate basis for modulating the volume of the stimulation (e.g., as the ratio increase, the intensity increases and vice versa). This concept is further illustrated in FIG. 7. FIG. 7 illustrates a ratio between convolutional layer value outputs used to modulate stimulation provided to a user (e.g., user 12 shown in FIG. 1). The top curve 700 shows the log (smoothed using a one minute long temporal window) of the ratio between the 6th 610 and the 7th 612 convolutional layer value outputs. A threshold on this ratio configured to indicate when to deliver stimulation is indicated by the dashed horizontal line 702. The threshold is determined by considering the distribution of the ratio in detected N3 sleep. The threshold is then set to ensure that a portion (e.g. 50%) of detected N3 sleep receives stimulation. In this example, the threshold is configured to prevent delivery of stimulation during shallow N3 sleep. The vertical lines 704 show the timing of the stimulation and the length of the lines correlates with the tone volume (in dBs), which may be proportional to an amount the determined ratio exceeds the threshold. For comparison, other system and non-system generated output curves 706, 708, and 710 are illustrated. Curve 706 is a soft output (e.g., determined as described above) curve showing the predicted probability of various sleep stages. Curve 708 is a hard output (e.g., determined as described above) predicted sleep stage curve. Curve 710 shows manually annotated sleep stages for the same period of sleep 712. Curves 706, 708, and 710 show less variation than curve 700. According to curves 706, 708, and 710, a user is in N3 sleep for a majority of sleep period 712. Reliance on curves 706, 708, or 710 could cause system 10 (e.g., model component 32, control component 34, and/or modulation component 36) to deliver too much stimulation, and/or stimulation with too much intensity because the user appears to be in steady N3 sleep. This may unintentionally wake a user, for example.

In some embodiments, modulation component 36 (FIG. 1) is configured to weight one or more of the brain activity parameters, the values output from the one or more convolutional layers, and the values output from the one or more recurrent layers relative to each other. In some embodiments, modulation component 36 is configured to cause the one or more sensory stimulators to modulate the sensory stimulation based on the weighted one or more brain activity parameters, the weighted values output from the one or more convolutional layers, and the weighted values output from the one or more recurrent layers. In the example shown in FIG. 7, modulation component 36 may weight the ratio between convolutional layer outputs more heavily than the soft or hard outputs 708 and 706 when determining how to modulate the stimulation delivered to user 12 (FIG. 1). Volume in this case is set according to:

$$\text{Volume} = \lambda \times \text{Ratio} + (1-\lambda) \times N3 \text{ probability}, \ 0 < \lambda < 1$$

The closer $\lambda$ is to 1, then the higher the importance of the Ratio on the volume is.

Returning to FIG. 1, in some embodiments, modulation component 36 is configured to modulate the sensory stimulation based on the brain activity parameters alone, which may be determined based on the output signals from sensors 14 (e.g., based on a raw EEG signal). In these embodiments, the output of a deep neural network (and/or other machine learning models) continues to be used to predict sleep stages (e.g., as described above). However, the stimulation intensity (e.g., volume) and timing is instead modulated based on brain activity parameters determined based on the sensor output signals. The sensor output signals may be and/or include a raw EEG signal, and the brain activity parameters determined based on such a signal may include a ratio between the EEG delta and EEG beta power, for example. However, other sensor output signals and other brain activity parameters are contemplated.

Figure 8:
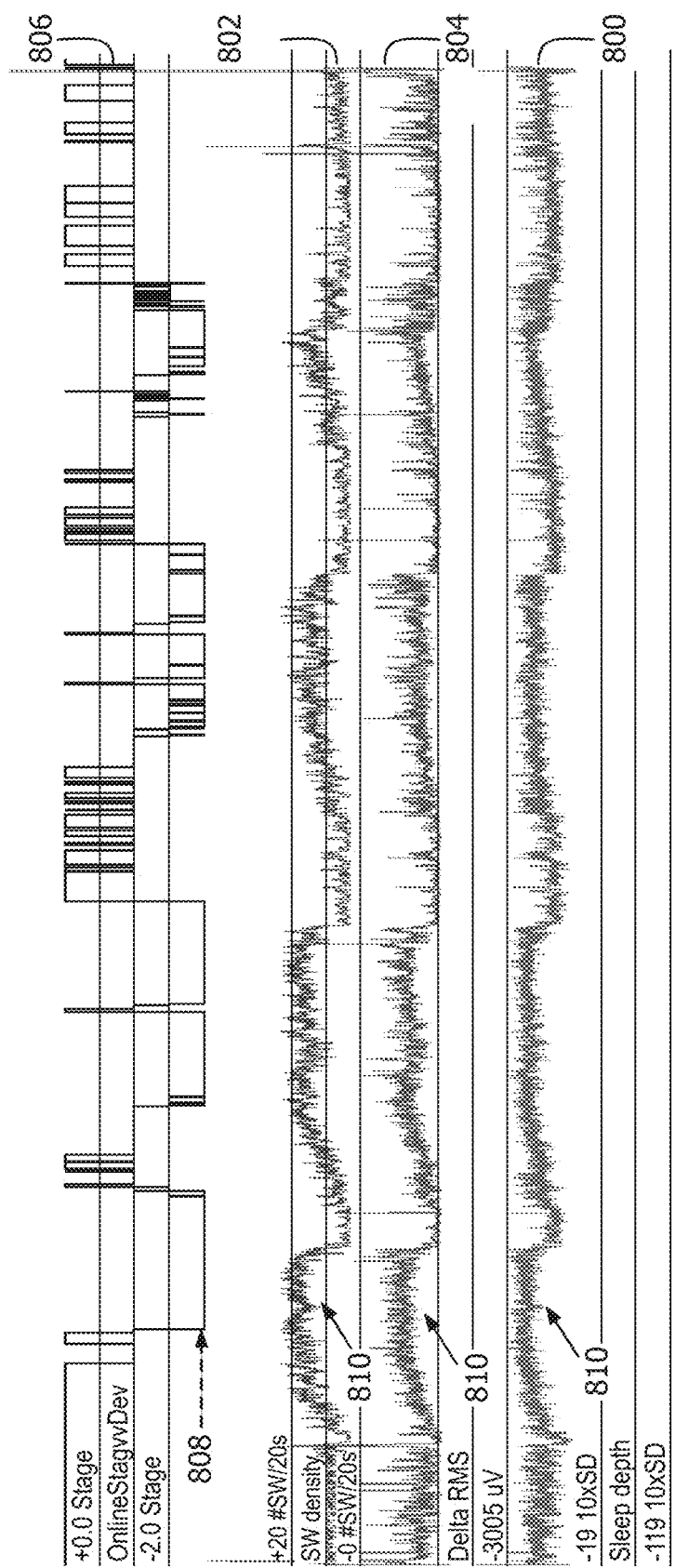
FIG. 8 illustrates brain activity parameters sleep depth, slow wave density, and delta power with respect to sleep stages for a sleep session, in accordance with one or more embodiments.
Figure 9:
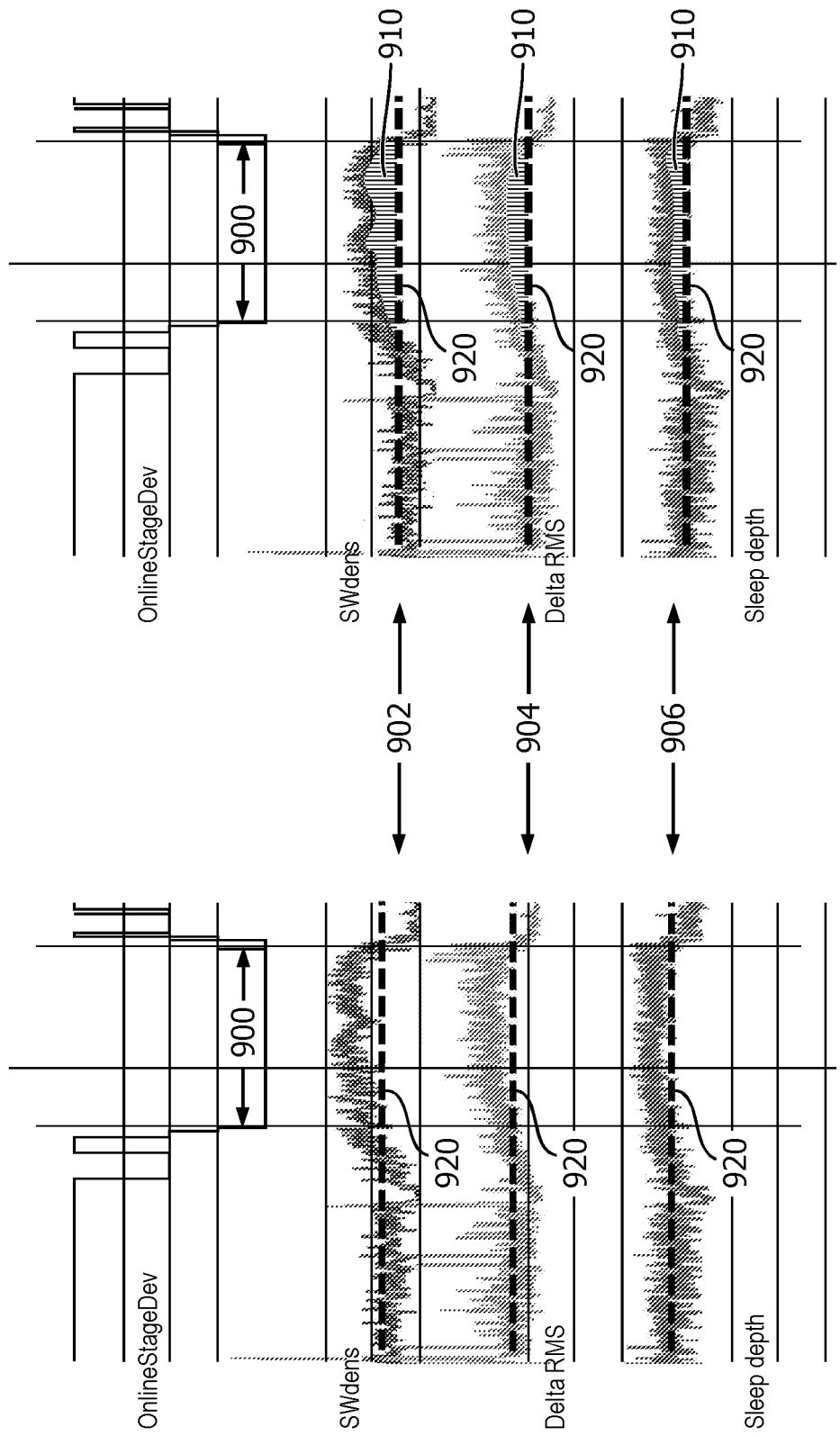
FIGS. 9A and 9B illustrate details of a period of N3 sleep, in accordance with one or more embodiments.

By way of a non-limiting example, FIG. 8 illustrates brain activity parameters sleep depth 800, slow wave density 802, and delta power 804 (in RMS units) with respect to sleep stages 806 for a sleep session. The sleep depth, slow wave density, and delta power may be determined based on a raw EEG signal, for example. As shown in FIG. 8, curves 800-806 generally correspond to each other. When the sleep stage is a deeper sleep stage 808, sleep depth 800, slow wave density 802, and delta power 804 generally show a corresponding increase 810. The opposite is also true. This holds across sleep cycles. A sleep cycle is clearly visible as an inverse-U shape in the sleep-depth, slow wave density, and delta power curves.

FIGS. 9A and 9B illustrate details of a period 900 of N3 sleep. In FIGS. 9A and 9B, the dynamics of features from a raw EEG signal are again visible (similar to those shown in FIG. 8). FIGS. 9A and 9B illustrate sleep depth 906, slow wave density 902, and delta power 904 (in RMS units) for period 900. These parameters are illustrated in FIG. 9A and again in 9B. FIG. 9B also indicates the timing and intensity of stimulation 910 (auditory tones in this example) delivered to a user (e.g., user 12 shown in FIG. 1). The spacing and length of the individual vertical lines indicates timing and intensity respectively. Modulation component 36 (FIG. 1) may be configured to control the stimulation based on any one of these features individually, for example, or some combination of two or more of these features. For the highlighted detected N3 sections 900, modulation component 36 is configured such that the tone volume (in this example) is proportional to a given EEG feature. Model component 32 (FIG. 1) and/or control component 34 (FIG. 1) may be configured such that optional lower threshold 920 for an individual feature 902, 904, 906 is used to prevent delivery of tones in shallower N3 sleep, for example. Again, this holds across sleep cycles.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via user interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and user 12, and/or other users through which user 12 and/or other users may provide information to and receive information from system 10. This enables data, cues, results, and/or instructions and any other communicable items, collectively referred to as "information," to be communicated between a user (e.g., user 12) and one or more of sensor 14, sensory stimulator 16, external resources 18, processor 20, and/or other components of system 10. For example, a hypnogram, EEG data, sleep stage probability, and/or other information may be displayed for user 12 or other users via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 10:
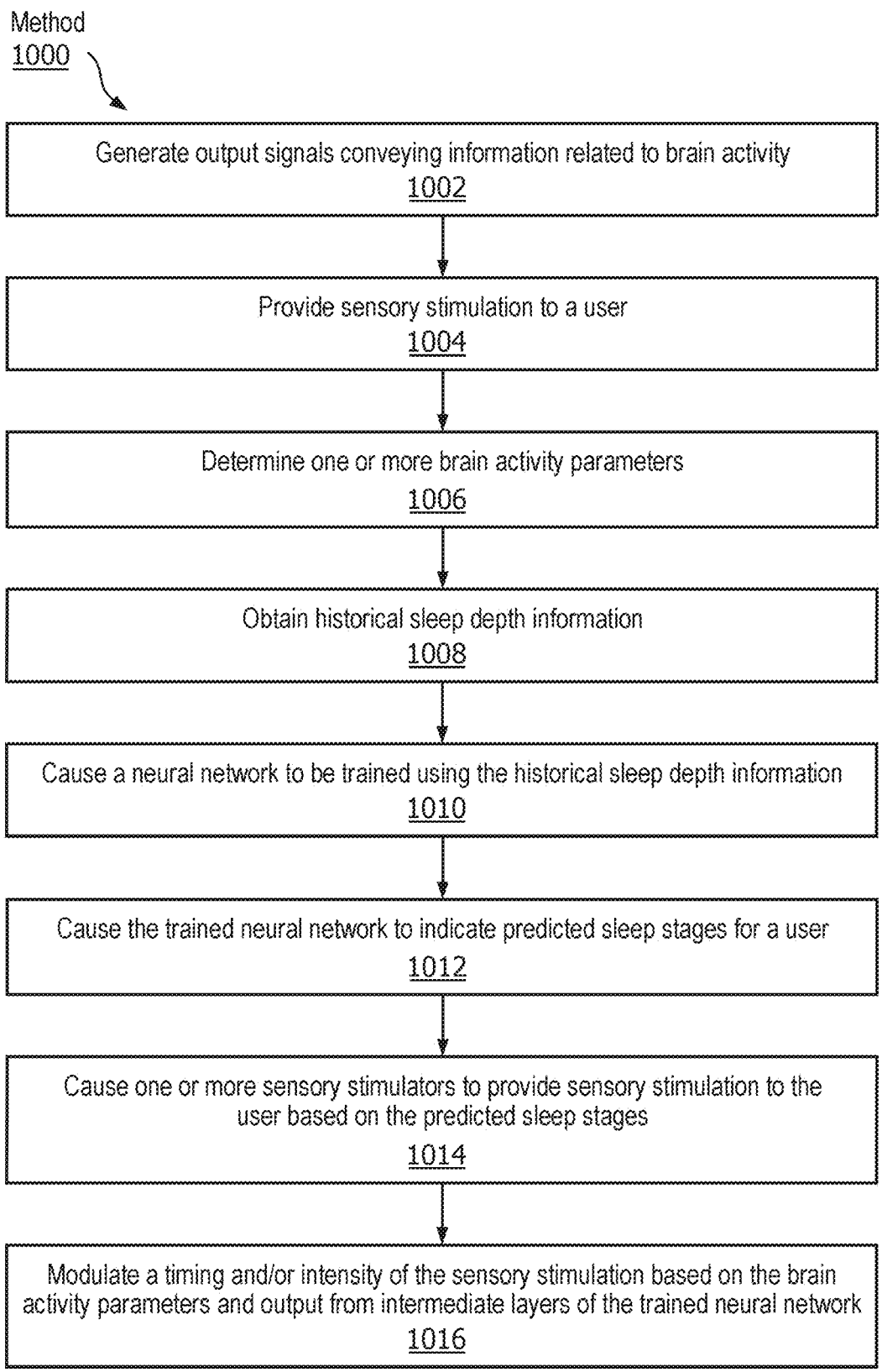
FIG. 10 illustrates method for delivering sensory stimulation to a user during a sleep session with a delivery system, in accordance with one or more embodiments.

FIG. 10 illustrates method 1000 for delivering sensory stimulation to a user during a sleep session with a delivery system. The system comprises one or more sensors, one or more sensory stimulators, one or more hardware processors configured by machine-readable instructions, and/or other components. The one or more hardware processors are configured to execute computer program components. The computer program components comprise an information component, a model component, a control component, a modulation component, and/or other components. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, output signals conveying information related to brain activity of a user are generated. The output signals are generated during a sleep session of the user and/or at other times. In some embodiments, operation 1002 is performed by sensors the same as or similar to sensors 14 (shown in FIG. 1 and described herein).

At an operation 1004, sensory stimulation is provided to a user. The sensory stimulation is provided during the sleep session and/or at other times. In some embodiments, operation 1004 is performed by sensory stimulators the same as or similar to sensory stimulators 16 (shown in FIG. 1 and described herein).

At an operation 1006, one or more brain activity parameters are determined. The brain activity parameters are determined based on the output signals and/or other information. The brain activity parameters indicate depth of sleep in the user. In some embodiments, operation 1006 is performed by a processor component the same as or similar to information component 30 (shown in FIG. 1 and described herein).

At an operation 1008, historical sleep depth information is obtained. The historical sleep depth information is for a population of users. The historical sleep depth information is related to brain activity of the population of users that indicates sleep depth over time during sleep sessions of the population of users. In some embodiments, operation 1008 is performed by a processor component the same as or similar to information component 30 (shown in FIG. 1 and described herein).

At an operation 1010, a neural network is trained using the historical sleep depth information. The neural network is trained based on the historical sleep depth information by providing the historical sleep depth information as input to the neural network. In some embodiments, training the neural network comprises causing the neural network to be trained. In some embodiments, operation 1010 is performed by a processor component the same as or similar to model component 32 (shown in FIG. 1 and described herein).

At an operation 1012, the trained neural network is caused to indicate predicted sleep stages for the user. This may be and/or include the trained neural network predicting future times during the sleep session at which the user will be in a deep sleep stage. The trained neural network is caused to indicate predicted sleep stages for the user and/or future times at which the user will be in deep sleep based on the output signals and/or other information. The trained neural network is configured to indicate sleep stages predicted to occur at future times for the user during the sleep session. The trained neural network comprises one or more intermediate layers. The one or more intermediate layers of the trained neural network include one or more convolutional layers and one or more recurrent layers of the trained neural network. The predicted sleep stages indicate whether the user is in deep sleep for stimulation and/or other information.

In some embodiments, operation 1012 includes providing the information in the output signals to the neural network in temporal sets that correspond to individual periods of time during the sleep session. In some embodiments, operation 1012 includes causing the trained neural network to output the predicted sleep stages and/or the future times of predicted deep sleep for the user during the sleep session based on the temporal sets of information. In some embodiments, operation 1012 is performed by a processor component the same as or similar to model component 32 (shown in FIG. 1 and described herein).

At an operation 1014, the one or more sensory stimulators are caused to provide sensory stimulation to the user based on the predicted timing of deep sleep stages during the sleep session and/or other information. The one or more sensory stimulators are caused to provide the sensory stimulation to the user responsive to the predicted sleep stages and/or the future times indicating the user will be in deep sleep for stimulation. In some embodiments, operation 1014 is performed by a processor component the same as or similar to control component 34 (shown in FIG. 1 and described herein).

At an operation 1016, the one or more sensory stimulators are caused to modulate a timing and/or intensity of the sensory stimulation based on the one or more brain activity parameters and values output from the one or more intermediate layers of the trained neural network. The one or more sensory stimulators are caused to modulate the timing and/or intensity of the sensory stimulation based on the one or more brain activity parameters, the value output from the one or more convolutional layers, and the values output from the one or more recurrent layers. In some embodiments, the values output from the one or more convolutional layers comprise two or more individual values output from two or more corresponding convolutional layers. In some embodiments, operation 1016 includes determining a ratio of a value output from one convolutional layer to a value output from another convolutional layer. In some embodiments, operation 1016 includes causing the one or more sensory stimulators to modulate the timing and/or intensity of the sensory stimulation based on the ratio.

In some embodiments, operation 1016 includes weighting the one or more brain activity parameters, the values output from the one or more convolutional layers, and the values output from the one or more recurrent layers relative to each other. In some embodiments, operation 1016 includes causing the one or more sensory stimulators to modulate the sensory stimulation based on the weighted one or more brain activity parameters, the weighted values output from the one or more convolutional layers, and the weighted values output from the one or more recurrent layers.

In some embodiments, the sensory stimulation comprises audible tones. Causing the one or more sensory stimulators to modulate the timing and/or intensity of the sensory stimulation comprises decreasing an inter tone interval and/or increasing a tone volume responsive to the one or more brain activity parameters and/or the values output from the one or more intermediate layers indicating the user is in deep sleep. In some embodiments, operation 1016 is performed by a processor component the same as or similar to modulation component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to deliver sensory stimulation to a user during a sleep session, the system comprising:
   one or more sensors configured to generate output signals conveying information related to brain activity of the user during the sleep session;
   one or more sensory stimulators configured to provide the sensory stimulation to the user during the sleep session; and
   one or more hardware processors coupled to the one or more sensors and the one or more sensory stimulators, the one or more hardware processors configured by machine-readable instructions to:
      obtain historical sleep depth information for a population of users, the historical sleep depth information being related to brain activity of the population of users that indicates sleep depth over time during sleep sessions of the population of users;

cause a neural network to be trained based on the historical sleep depth information by providing the historical sleep depth information as input to the neural network;

cause, based on the output signals, the trained neural network to predict future times during the sleep session at which the user will be in a deep sleep stage, the trained neural network comprising an input layer, an output layer, and one or more intermediate layers between the input layer and the output layer;

determine, with respect to each of the future times, one or more values generated by the one or more intermediate layers of the trained neural network; and cause the one or more sensory stimulators to provide the sensory stimulation to the user at the future times and to modulate a timing and/or intensity of the sensory stimulation during the sleep session based on the one or more values of the one or more intermediate layers.

2. The system of claim 1, wherein the one or more hardware processors are further configured to determine one or more brain activity parameters of the user based on the output signals, the one or more brain activity parameters indicative of sleep depth in the user; and cause the one or more sensory stimulators to modulate the timing and/or intensity of the sensory stimulation during the sleep session based on the one or more values of the one or more intermediate layers and the one or more brain activity parameters.

3. The system of claim 2, wherein the one or more hardware processors are configured such that the one or more values from the one or more intermediate layers of the trained neural network include values from one or more convolutional layers and values from one or more recurrent layers of the trained neural network, and the one or more sensory stimulators are caused to modulate the timing and/or intensity of the sensory stimulation based on the one or more brain activity parameters, the values from the one or more convolutional layers, and the values from the one or more recurrent layers.

4. The system of claim 3, wherein the one or more hardware processors:
(i) are configured such that the values from the one or more convolutional layers comprise two or more individual values from two or more corresponding convolutional layers,
(ii) determine a ratio of a value from one convolutional layer to a value from another convolutional layer, and
(iii) cause the one or more sensory stimulators to modulate the timing and/or intensity of the sensory stimulation based on the ratio.

5. The system of claim 3, wherein the one or more hardware processors are further configured to weight the one or more brain activity parameters, the values from the one or more convolutional layers, and the values from the one or more recurrent layers relative to each other, and cause the one or more sensory stimulators to modulate the sensory stimulation based on the weighted one or more brain activity parameters, the weighted values from the one or more convolutional layers, and the weighted values from the one or more recurrent layers.

6. The system of claim 1, wherein the one or more hardware processors are configured to provide the information in the output signals to the neural network in temporal sets that correspond to individual periods of time during the sleep session, and cause the trained neural network to predict the future times based on the temporal sets of information.

7. The system of claim 1, wherein the one or more sensory stimulators are configured such that the sensory stimulation comprises audible tones, and the one or more hardware processors are configured such that causing the one or more sensory stimulators to modulate the timing and/or intensity of the sensory stimulation comprises decreasing an inter tone interval and/or increasing a tone volume responsive to an indication the user is in deep sleep.

8. A method for delivering sensory stimulation to a user during a sleep session with a delivery system, the system comprising one or more sensors, one or more sensory stimulators, and one or more hardware processors coupled to the one or more sensors and the one or more sensory stimulators, the one or more processors configured by machine readable instructions, the method comprising:

generating, with the one or more sensors, output signals conveying information related to brain activity of the user during the sleep session;

providing, with the one or more sensory stimulators, the sensory stimulation to the user during the sleep session;

obtaining, with the one or more hardware processors, historical sleep depth information for a population of users, the historical sleep depth information being related to brain activity of the population of users that indicates sleep depth over time during sleep sessions of the population of users;

causing, with the one or more hardware processors, a neural network to be trained based on the historical sleep depth information by providing the historical sleep depth information as input to the neural network;

causing, with the one or more hardware processors, based on the output signals, the trained neural network to predict future times during the sleep session at which the user will be in a deep sleep stage, the trained neural network comprising an input layer, an output layer, and one or more intermediate layers between the input layer and the output layer;

determining, with the one or more hardware processors, with respect to each of the future times, one or more values generated by the one or more intermediate layers of the trained neural network; and causing, with the one or more hardware processors, the one or more sensory stimulators to provide the sensory stimulation to the user at the future times and to modulate a timing and/or intensity of the sensory stimulation during the sleep session based on the one or more values of the one or more intermediate layers.

9. The method of claim 8, further comprising determining, with the one or more hardware processors, one or more brain activity parameters of the user based on the output signals, the one or more brain activity parameters indicative of sleep depth in the user; and causing, with the one or more hardware processors, the one or more sensory stimulators to modulate the timing and/or intensity of the sensory stimulation during the sleep session based on the one or more values of the one or more intermediate layers and the one or more brain activity parameters.

10. The method of claim 9, wherein the one or more values from the one or more intermediate layers of the trained neural network include values from one or more convolutional layers and values from one or more recurrent layers of the trained neural network, and the one or more sensory stimulators are caused to modulate the timing and/or intensity of the sensory stimulation based on the one or more brain activity parameters, the values from the one or more convolutional layers, and the values from the one or more recurrent layers.

11. The method of claim 10, wherein the values from the one or more convolutional layers comprises two or more individual values from two or more corresponding convolutional layers, and wherein the method further comprises:
   determining, with the one or more hardware processors, a ratio of a value from one convolutional layer to a value from another convolutional layer, and
   causing, with the one or more hardware processors, the one or more sensory stimulators to modulate the timing and/or intensity of the sensory stimulation based on the ratio.

12. The method of claim 10, further comprising weighting, with the one or more hardware processors, the one or more brain activity parameters, the values from the one or more convolutional layers, and the values from the one or more recurrent layers relative to each other, and causing the one or more sensory stimulators to modulate the sensory stimulation based on the weighted one or more brain activity parameters, the weighted values from the one or more convolutional layers, and the weighted values from the one or more recurrent layers.

13. The method of claim 8, further comprising providing, with the one or more hardware processors, the information in the output signals to the neural network in temporal sets that correspond to individual periods of time during the sleep session, and causing the trained neural network to predict the future times based on the temporal sets of information.

14. The method of claim 8, wherein the sensory stimulation comprises audible tones, and causing the one or more sensory stimulators to modulate the timing and/or intensity of the sensory stimulation comprises decreasing an inter tone interval and/or increasing a tone volume responsive to an indication the user is in deep sleep.

15. A system for delivering sensory stimulation to a user during a sleep session, the system comprising:
   means for generating output signals conveying information related to brain activity of the user during the sleep session;
   means for providing the sensory stimulation to the user during the sleep session;
   means for obtaining historical sleep depth information for a population of users, the historical sleep depth information being related to brain activity of the population of users that indicates sleep depth over time during sleep sessions of the population of users;
   means for causing a neural network to be trained based on the historical sleep depth information by providing the historical sleep depth information as input to the neural network;
   means for causing, based on the output signals, the trained neural network to predict future times during the sleep session at which the user will be in a deep sleep stage, the trained neural network comprising an input layer, an output layer, and one or more intermediate layers between the input layer and the output layer;
   means for determining, with respect to each of the future times, one or more values generated by the one or more intermediate layers of the trained neural network; and
   means for causing the means for providing sensory stimulation to provide the sensory stimulation to the user at the future times and to modulate a timing and/or intensity of the sensory stimulation during the sleep session based on the one or more values of the one or more intermediate layers.

16. The system of claim 15, further comprising means for determining one or more brain activity parameters of the user based on the output signals, the one or more brain activity parameters indicative of sleep depth in the user; and causing the means for providing the sensory stimulation to modulate the timing and/or intensity of the sensory stimulation during the sleep session based on the one or more values of the one or more intermediate layers and the one or more brain activity parameters.

17. The system of claim 16, wherein the one or more values from the one or more intermediate layers of the trained neural network include values from one or more convolutional layers and values from one or more recurrent layers of the trained neural network, and the means for providing the sensory stimulation are caused to modulate the timing and/or intensity of the sensory stimulation based on the one or more brain activity parameters, the values from the one or more convolutional layers, and the values from the one or more recurrent layers.

18. The system of claim 17, wherein the values from the one or more convolutional layers comprises two or more individual values from two or more corresponding convolutional layers, and wherein the system further comprises:
   means for determining a ratio of a value from one convolutional layer to a value from another convolutional layer, and
   means for causing the means for providing the sensory stimulation to modulate the timing and/or intensity of the sensory stimulation based on the ratio.

19. The system of claim 17, further comprising means for weighting the one or more brain activity parameters, the values from the one or more convolutional layers, and the values from the one or more recurrent layers relative to each other, and causing the means for providing sensory stimulation to modulate the sensory stimulation based on the weighted one or more brain activity parameters, the weighted values from the one or more convolutional layers, and the weighted values from the one or more recurrent layers.

20. The system of claim 16, further comprising means for providing the information in the output signals to the neural network in temporal sets that correspond to individual periods of time during the sleep session, and causing the trained neural network to predict the future times based on the temporal sets of information.

21. The system of claim 16, wherein the sensory stimulation comprises audible tones, and causing the means for providing the sensory stimulation to modulate the timing and/or intensity of the sensory stimulation comprises decreasing an inter tone interval and/or increasing a tone volume responsive to an indication the user is in deep sleep.

* * * * *